(12) United States Patent
Chu et al.

(10) Patent No.: US 8,347,685 B1
(45) Date of Patent: Jan. 8, 2013

(54) METHOD AND DEVICE FOR VALIDATING OR CALIBRATING A CHEMICAL DETECTOR AT A POINT OF USE

(75) Inventors: Pamela M. Chu, Montgomery Village, MD (US); Jeffrey R. Anderson, Mount Airy, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 559 days.

(21) Appl. No.: 12/604,496

(22) Filed: Oct. 23, 2009

(51) Int. Cl.
*G01N 35/10* (2006.01)
(52) U.S. Cl. ..... 73/1.06; 73/1.02; 73/864.82; 73/864.85
(58) Field of Classification Search ................ 73/1.06, 73/864.82, 864.85
See application file for complete search history.

(56) References Cited

U.S. PATENT DOCUMENTS

| | | | | |
|---|---|---|---|---|
| 1,905,362 A * | 4/1933 | Blaivas | ................. | 604/403 |
| 6,912,924 B2 * | 7/2005 | Loomis et al. | ................. | 73/865.9 |
| 7,260,976 B2 * | 8/2007 | Colman et al. | ................. | 73/1.06 |
| 7,306,765 B2 * | 12/2007 | Davis et al. | ................. | 422/62 |
| 2006/0078477 A1 * | 4/2006 | Althouse et al. | ................. | 422/123 |

* cited by examiner

*Primary Examiner* — Hezron E Williams
*Assistant Examiner* — Paul West
(74) *Attorney, Agent, or Firm* — Ulysses John Biffoni (57) ABSTRACT

A method for validating or calibrating a chemical detector at a point of use. The method includes presenting a device to the chemical detector, the device comprising a frangible container defining a predetermined volume and a chemical material sealed within the frangible container in a predetermined amount, and breaking the frangible container to release the chemical material for detection by the chemical detector. A device and method of making the device for validating or calibrating a chemical at a point of use are also provided.

27 Claims, 7 Drawing Sheets

METHOD AND DEVICE FOR VALIDATING OR CALIBRATING A CHEMICAL DETECTOR AT A POINT OF USE

GOVERNMENTAL INTEREST

The invention described herein may be manufactured, used and licensed by or for the U.S. Government.

BACKGROUND

The present invention relates generally to a simple, low-cost method and device for presenting a known amount of a volatile or semi-volatile chemical material to a chemical detector, thus enabling an end user to quickly verify that a chemical detector is functioning properly or to calibrate the chemical detector.

Commercial chemical vapor detectors are commonly used to identify the presence and quantity of specific chemicals. Some chemical detectors may, for example, pull a sample of ambient air into the detection system for analysis. Test samples with known composition are important for verifying that the chemical detectors are functioning properly. Methods and devices for verifying and calibrating such chemical detectors are necessary in a variety of industries, including the defense, homeland security, environmental monitoring, industrial monitoring and health related industries.

Known methods for generating well characterized gas concentration samples to test the chemical detectors are typically costly, time-consuming and difficult to use without prior experience. These traditional methods do not allow a user to test a chemical detector at a point of use where it is critical for a soldier or a first responder to ensure that chemical detectors are operational and will alarm in the presence of toxic chemical vapors.

SUMMARY

In an exemplary embodiment of the invention there is provided a method for validating or calibrating a chemical detector at a point of use. The method may include presenting a device to the chemical detector, the device comprising a frangible container defining a predetermined volume and a chemical material sealed within the frangible container in a predetermined amount; and breaking the frangible container to release the chemical material for detection by the chemical detector.

Another embodiment provides a method for making a device to validate or calibrate a chemical detector at a point of use. The method may include supplying a predetermined amount of chemical material to a frangible container, the frangible container having first and second tubes coupled thereto at a first end, each of the first and second tubes having a second free end to define, a substantially u-shaped vessel. The method may include sealing the second free ends of the first and second tubes.

In another embodiment of the invention, a device for validating or calibrating a chemical detector at a point of use is provided. The device may include a frangible container defining a predetermined volume. A chemical material may be disposed within the frangible container in a predetermined amount. First and second tubes each having a first end may be coupled to the frangible container and a second free end to define a substantially u-shaped vessel. Each second end of the first and second tubes may be sealed.

This summary is provided merely to introduce certain concepts and not to identify any key or essential features of the claimed subject matter. Further features and advantages of the invention, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of an embodiment of the invention, as illustrated in the accompanying drawings wherein like reference numbers generally indicate identical, functionally similar, and/or structurally similar elements. Unless otherwise indicated, the accompanying drawing figures are not to scale.

DETAILED DESCRIPTION

Various embodiments of the invention are discussed herein. While specific embodiments are discussed, specific terminology is employed for the sake of clarity. However, the invention is not intended to be limited to the specific terminology so selected and it should be understood that this is done for illustration purposes only. A person skilled in the relevant art will recognize that other components and configurations can be used without parting from the spirit and scope of the invention defined by the claims. Each specific element includes all technical equivalents that operate in a similar manner to accomplish a similar purpose.

Figure 1:
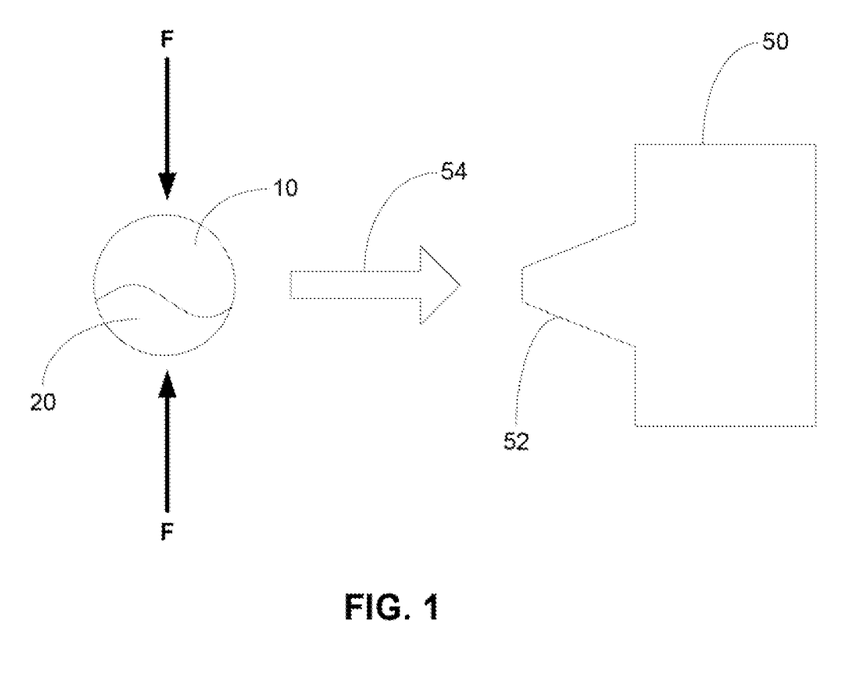
FIG. 1 depicts a cross-sectional diagram of the method for validating or calibrating a chemical detector at a point of use according to an embodiment of the invention.

Referring now to the drawings, there is shown in FIG. 1 a cross-sectional diagram of the method for validating or calibrating a chemical detector at a point of use according to an embodiment of the invention. The method may include presenting a frangible container 10 to a chemical detector 50. The frangible container 10 may define a predetermined volume and a chemical material 20 may be sealed within the frangible container 10 in a predetermined amount. The frangible container 10, storing the chemical material 20, may be presented (see arrow 54) to a sampling nozzle 52 of the chemical detector 50. One or more forces F may be applied to the frangible container 10 to rupture the frangible container 10 and release the chemical material 20. The chemical material 20 may trigger a threshold alarm level of the chemical detector 50. Thus, presenting the chemical material 20 in close proximity to the sampling nozzle 52 may allow for the validation or calibration of the chemical detector 50.

Figure 2:
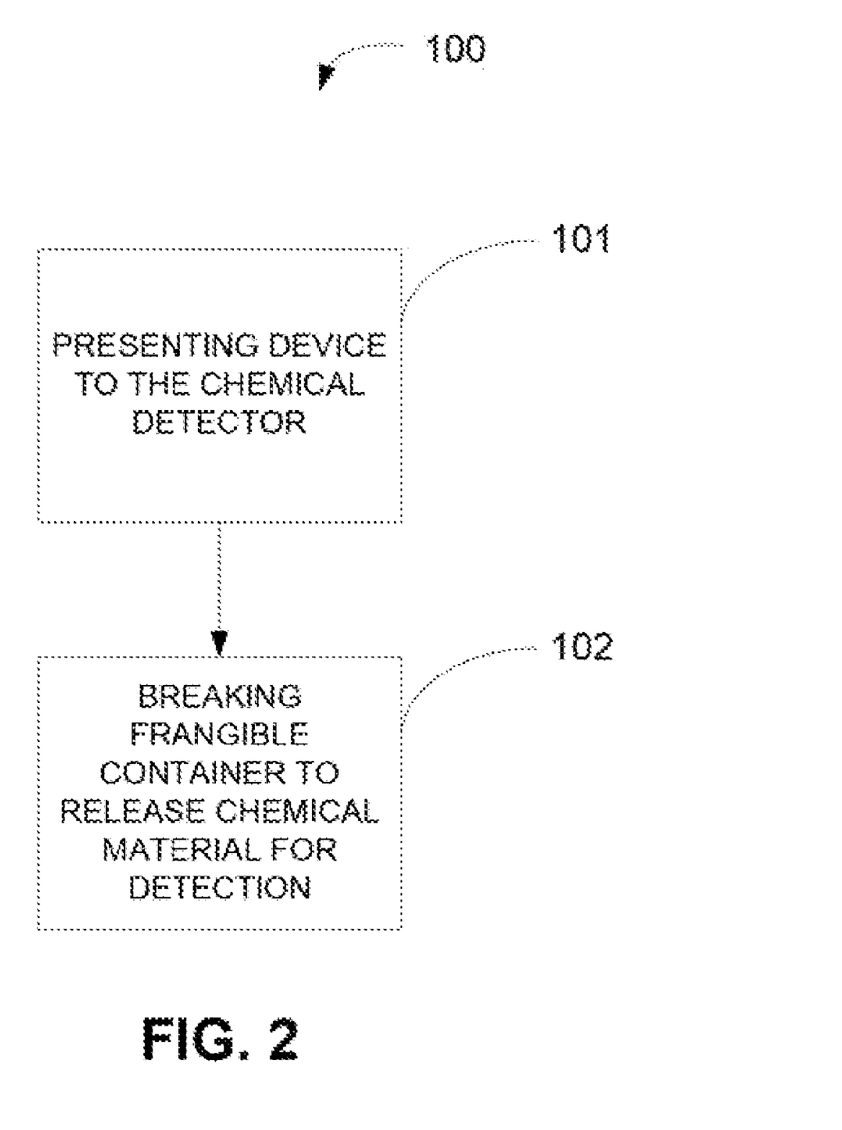
FIG. 2 depicts a flow chart of a method for validating or calibrating a chemical detector at a point of use according to an embodiment of the invention.

FIG. 2 depicts a flow chart of the method for validating or calibrating a chemical detector at a point of use according to an embodiment of the invention. The method 100 may include a first step 101 of presenting a device to the chemical detector 50. Using the example described above, the device may include a frangible container 10 defining a predetermined volume and a chemical material 20 sealed within the frangible container 10 in a predetermined amount. Similarly, the device may be, for example, but not limited to, the device 200 shown in FIGS. 3-6 and described in further detail below. The method may include a second step 102 of breaking the frangible container 10 at the point of use to release the chemical material 20 for detection by the chemical detector 50. Within a short time, depending on the volume of the chemical material 20 used and the sampling speed of the chemical detector 50, chemical vapors may evaporate from the deposited chemical material 20 and may be introduced into the chemical detector 50 for calibration or validation.

Figure 6:
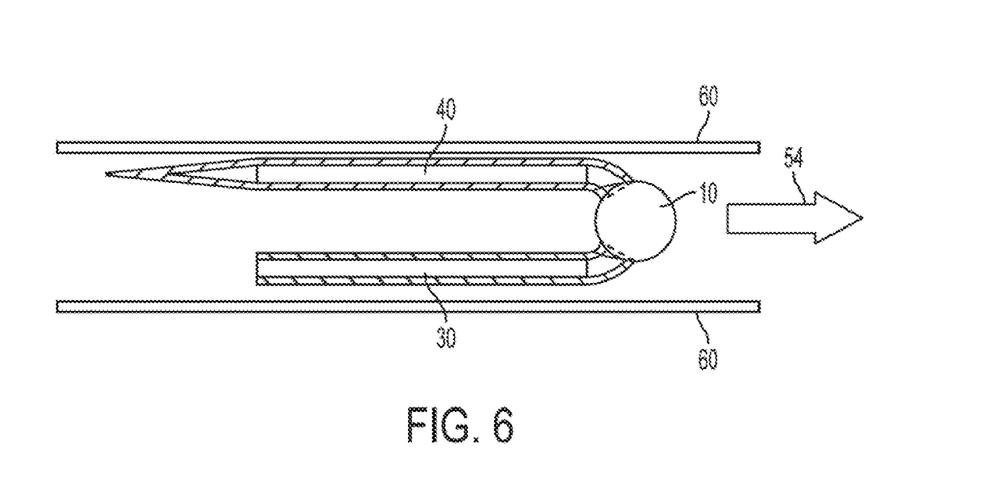
FIG. 6 depicts a cross-sectional view of the device positioned in flexible tubing according to an alternative embodiment of the invention.

According to an example embodiment shown in FIG. 6, the device may include a length of flexible tubing and the frangible container 10 may be disposed within the flexible tubing. According to this embodiment, the first step 101 of method 100 may include coupling an end of the flexible tubing to a sampling nozzle 52 of the chemical detector 50.

Alternatively, the method 100 of FIG. 2 may further include both the steps of inserting the device into a length of flexible tubing to cause the frangible container 10 to be disposed within the flexible tubing and coupling an end of the flexible tubing to a sampling nozzle 52 of the chemical detector 50.

According to another embodiment, following the second step 102, the released chemical material 20 may contact a wicking material (see FIG. 5) surrounding the broken frangible container 10 to introduce chemical vapors to the chemical detector 50 for validation.

Figure 3:
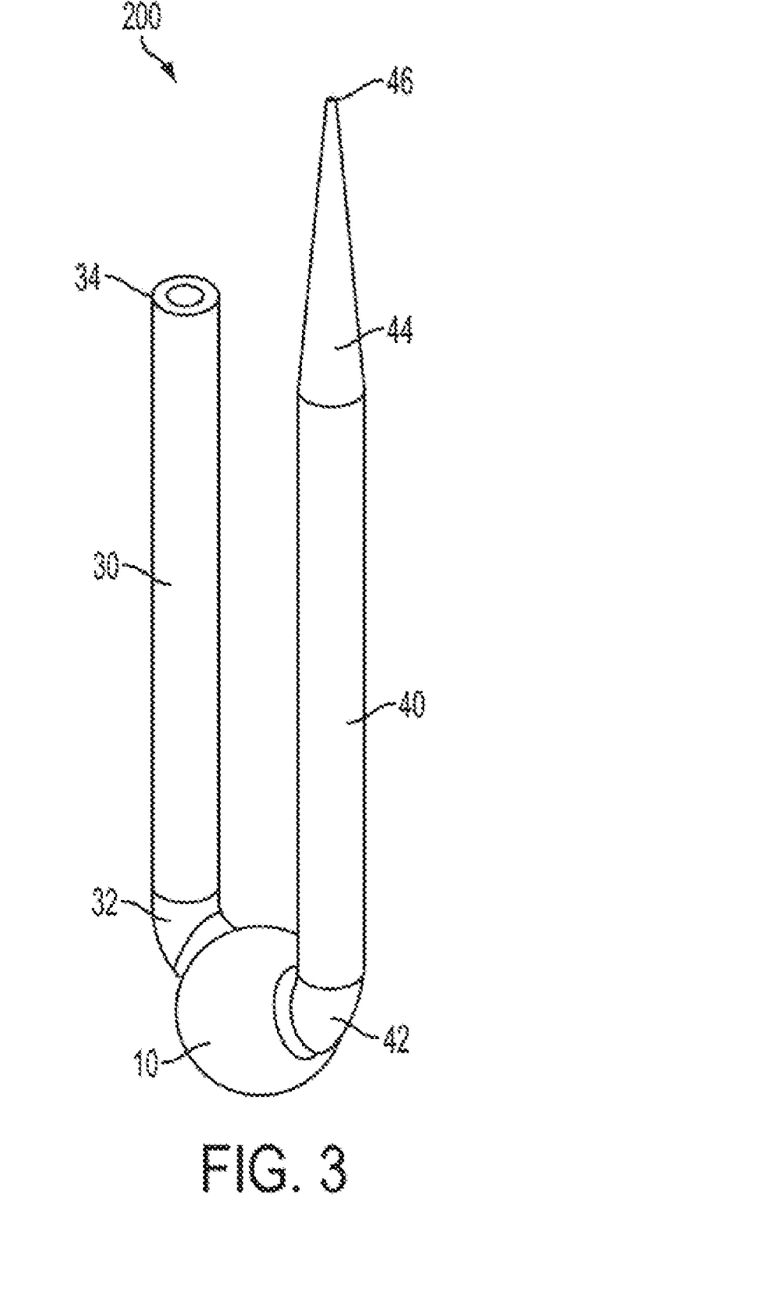
FIG. 3 depicts a perspective view of a device for validating or calibrating a chemical detector at a point of use according to an embodiment of the invention.
Figure 4:
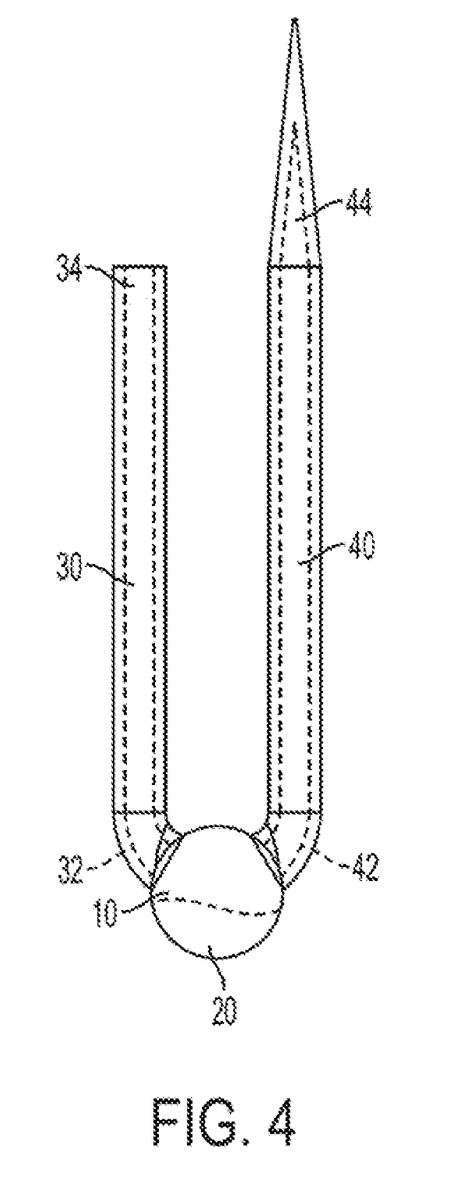
FIG. 4 depicts a front view of the device for validating or calibrating a chemical detector at a point of use according to an embodiment of the invention.

According to an example embodiment shown in FIG. 3, the device may include a first and second tube 30, 40 each having a first end 32, 42 coupled to the frangible container 10 and a second free end 34, 44 to define a substantially u-shaped vessel. Each second end 34, 44 may be sealed and the second step 102 of the method 100 may include squeezing the first and second tubes 30, 40 together to rupture the frangible container 10 and release the chemical material 20. In this exemplary embodiment, the action of squeezing the first and second tubes 30, 40 may shatter the frangible container 10, for example a thin glass bulb, whereas a simple small frangible container 10 alone may otherwise be difficult to break.

The predetermined amount of chemical material 20 may be sufficient to meet a threshold alarm level of the chemical detector 50. The ultimate accuracy of the method 100 may be largely determined by the volume measurement of the chemical material 20 introduced into the frangible container 10. The predetermined volume of the chemical material 20 may be a known amount of a well-analyzed sample. The volume measurement may also be sufficient to meet most accuracy requirements for field measurements.

In general, the method 100 may assure that target concentrations of materials are delivered within acceptable uncertainties, may provide for simple use, may be capable of delivering sub-nanoliter volumes of test chemicals, may be compatible with reactive and/or semi-volatile liquids, may be low cost, and may provide a long lifetime of the chemical sample and the delivery device (for example, greater than 10 years).

FIGS. 3-6 depict various views of a device for validating or calibrating a chemical detector at a point of use according to an embodiment of the present invention. As shown in FIG. 3, the device 200 includes a frangible container 10 defining a predetermined volume, a chemical material 20 disposed within the frangible container 10 in a pre-determined amount, and first and second tubes 30, 40 each having a first end 32, 42 coupled to the frangible container 10 and a second free end 34, 44 to define a substantially u-shaped vessel. Prior to using the device 200, each second end 34, 44 of the first and second tubes 30, 40 may be sealed.

The predetermined amount of chemical material 20 may be sufficient to meet a threshold alarm level of the chemical detector 50. Specific chemical materials 20, for example liquid solutions, may be optimized for the particular detector technology and alarm concentration levels. For example, to test a M4 JCAD chemical agent detector a dilute solution of methyl salicylate (i.e. a blister agent simulant for an ion mobility spectrometer) in methanol may be used to produce sufficient concentrations of methyl salicylate to trigger the chemical detector alarm.

According to an embodiment, the second end 44 of the second tube 40 may be tapered. The second end 44 may also be trimmed to include a small vent hole 46 prior to sealing. Dissimilarly, the first tube 30 may maintain a constant inner and outer diameter to serve as a passage for the supply of chemical material 20 to the frangible container 10 during manufacture.

According to another embodiment, the first and second tubes 30, 40 may have an inner diameter large enough to prevent the chemical material 20 from remaining in the first or second tubes 30, 40 by capillary action. For example, the first and second tubes 30, 40 may each be about 2.5 centimeters long and the inner and outer diameters may be about 0.1 centimeters and 0.2 centimeters, respectively.

According to an embodiment, the frangible container 10 may be glass to give chemical stability to the system. For example, the frangible container 10 may be an approximately spherical glass bulb. According to a further embodiment, the predetermined volume of the frangible container 10 may be approximately 50 micro-liters with a wall thickness of approximately 0.1 millimeters.

According to one embodiment, the predetermined amount of the chemical material 20 may be between approximately 5 micro-liters and 100 micro-liters. For applications which require the use of sub-nanoliter volumes, dilution of the liquid sample in an appropriate solvent may be a potential approach. According to one example, the predetermined amount of the chemical material 20 may be approximately 20 micro-liters and may fill a frangible container 10 having a predetermined volume of approximately 50 micro-liters.

According to another embodiment, the chemical material 20 may be a liquid chemical material or a gaseous material. Stated another way, any liquid chemical, or mixture of liquid chemicals, having a sufficient vapor pressure to produce the desired concentrations to trigger a threshold alarm level of the chemical detector may be used as the chemical material 20. For example, the chemical material 20 may be a volatile or semi-volatile chemical material or compound.

Examples of liquid chemical materials may include, but are not limited to, methanol, ethanol, isopropyl alcohol, iso-butyl alcohol, acetone, acetonitrile, benzaldehyde, benzene, toluene, xylene, carbon tetrachloride, carbon disulfide, dimethyl sulfide, mercury, bromine, iso-butyl mercaptan, chloroform, dimethyl methyl phosphonate, dichloromethane, dimethyl disulfide, ethyl benzene, ethyl chloride, ethyl mercaptan, ethyl methyl sulfide, hexane, hydrazine, methyl iodide, isopropyl alcohol, propylene oxide, isopropyl mercaptan, thiophene, water, acrolein, acrylonitrile, etc.

Examples of gaseous chemical materials may include, but are not limited to, Ammonia, arsine, carbon dioxide, carbon monoxide, chlorine, hydrogen fluoride, freons, hydrogen sulfide, methyl bromide, methyl chloride, nitrogen dioxide, sulfur dioxide, sulfur hexafluoride, boron trichloride, carbonyl sulfide, ethylene, ethylene oxide, hydrogen chloride, methane, nitric oxide, nitrous oxide, oxygen, phosgene, phosphine, vinyl chloride, hydrogen cyanide, cyanogens chloride, arsine, etc. In comparison to a liquid chemical material, a larger frangible container 10 may be required to contain a gaseous chemical material.

According to a further embodiment, the chemical material 20 may be a solid or semi-volatile solid chemical material if such solid material produces a sufficient vapor pressure to trigger a threshold alarm level of the chemical detector 50. Examples of solid chemical materials may include, but are not limited to, formaldehyde or phenol.

Figure 5:
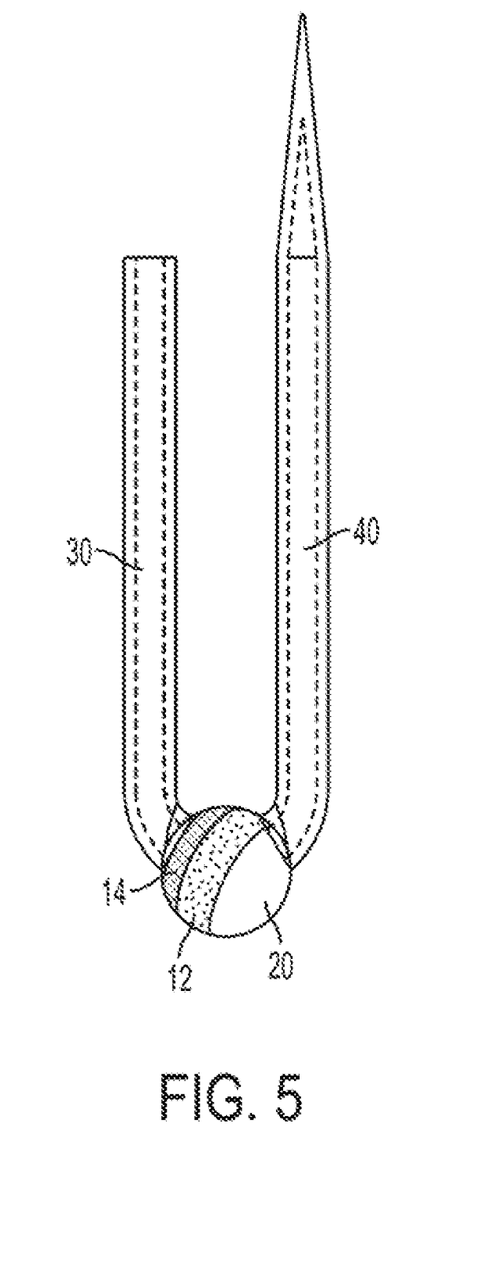
FIG. 5 depicts a front view of the device for validating or calibrating a chemical detector at a point of use, including a wick and mesh material, according to an alternative embodiment of the invention.

As shown in FIG. 5, if the chemical material 20 is a liquid chemical material, the device 200 may further include a wick material 12 surrounding the frangible container 10. The wick material 12 may be adapted to wick the liquid chemical material 20 after the first and second tubes 30, 40 are squeezed together to break the frangible container 10 and release the liquid chemical material 20. The wick material 12 may provide a large surface area for evaporation of the chemical material 20. Additionally, the wick material may also be adapted to contain the broken fragments of the frangible container 10 after release of the liquid chemical container 20.

According to another embodiment, the device 200 may include a mesh material 14 surrounding the frangible container 10 to contain broken fragments of the frangible container 10 after release of the chemical material 20. For example, the mesh material 14 may be a polymer mesh. The wick material 12 and/or mesh material 14 may surround the entire device 200, thus encasing both the frangible container 10 and first and second tubes 30, 40.

As shown in FIG. 6, the device 200 may include a length of flexible tubing 60. The frangible container 10 may be disposed within the flexible tubing 60 and the flexible tubing 60 may be configured to be attachable to a sampling nozzle 52 of a chemical detector 50. The flexible tubing 60 may be configured to ensure that the frangible container 10 is positioned in a consistent position and/or proximity to the chemical detector 50. Such a configuration may aid in producing consistent detection and/or calibration results.

Figure 7:
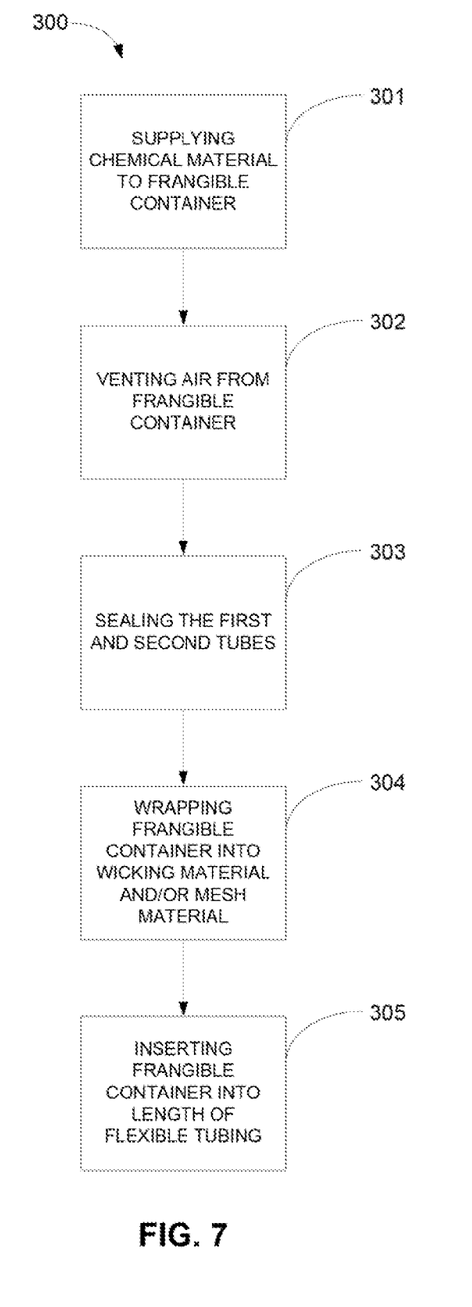
FIG. 7 depicts a flow chart of a method for making a device to validate or calibrate a chemical detector at a point of use according to an embodiment of the invention.

FIG. 7 depicts a flow chart of a method for making a device to validate or calibrate a chemical detector at a point of use according to an embodiment of the invention. The method 300 may include a step 301 of supplying a predetermined amount of chemical material 20, sufficient to trigger a threshold alarm level of the chemical detector 50, to a frangible container 10. In this embodiment, the frangible container 10 may include first and second tubes 30, 40 coupled to the frangible container 10 at a first end 32, 42. Additionally, each of the first and second tubes 30, 40 may have a second free end 34, 44 to define a substantially u-shaped vessel. The method 300 may include the step 303 of sealing the second free ends 34, 44 of the first and second tubes 30, 40 to seal the frangible container 10.

According to one embodiment, the step 301 of supplying a predetermined amount of chemical material 20 to the frangible container 10 may occur through the first tube 30. This embodiment may include the additional step 302 of venting air from the frangible container 10 through an air vent 46 in the second tube 40 prior to sealing. The air vent 46 may be an opened, tapered or trimmed vent hole or aperture. The use of the first and second tubes 30, 40 may enable the frangible container 10 to be sealed without significantly heating the chemical material 20, thus minimizing any potential loss of the chemical material 20. Further, use of the first and second tubes 30, 40, as described above, may alleviate pressure in the device 200 by allowing air and heat to vent during the sealing process to prevent the frangible container 10 from over-heating, cracking or breaking prior to use.

According to another embodiment, the step 303 of sealing includes sealing the second free end 34 of the first tube 30 and immediately thereafter sealing the second free end 44 of the second tube 40. This enables the device 200 to be quickly sealed and to maintain the exact predetermined amount of chemical material 20 supplied.

According to a further embodiment, the method 300 may include the step 304 of wrapping the frangible container 10 into at least one of a wicking material or a mesh material. Step 304 may occur before or after the step 301 of supplying chemical material 20 to the frangible container 10. Additionally, the method 300 may include the step 305 of inserting the frangible container 10 into a length of flexible tubing 60, such as that depicted in FIG. 6.

According to another embodiment, the method 300 may include the step (not shown) of making the frangible container 10 prior to step 301 of supplying chemical material 20 to the frangible container 10.

The various embodiments of the invention, as described above, may allow users of chemical detectors to quickly validate instruments with little preparation, equipment and training. Such chemical detectors may include, but are not limited to, nerve gas chemical detectors, chemical warfare agent detectors, toxic industrial chemical (TICS) detectors, general industrial gas detectors, etc. The device may be handheld, miniaturized and light-weight to enable easy usage. Further, the device may be environmentally friendly and disposable after use in the field. The device for validating or calibrating a chemical detector at a point of use, as described above, may provide an inexpensive and technically simple alternative to many established methods for generating gas samples at specific levels.

While several embodiments of the invention are described above, it should be understood that the foregoing is presented by way of example only, and not limitation. Thus, the breadth and scope of the invention should not be limited by the above-described embodiments, but should instead be defined only in accordance with the following claims and their equivalents.

What is claimed is:

1. A method for validating or calibrating a chemical detector at a point of use, comprising:
   presenting a device to the chemical detector, the device comprising a frangible container defining a predetermined volume and a chemical material sealed within the frangible container in a predetermined amount, wherein said predetermined amount of the chemical material is between approximately 5 microliters and approximately 100 microliters; and wherein the device includes first and second tubes each having a first end coupled to the frangible container and a second free end to define a substantially u-shaped vessel, wherein each second end is sealed; and
   breaking the frangible container to release the chemical material for detection by the chemical detector, wherein the step of breaking comprises squeezing the first and second tubes together to rupture the frangible container and release the chemical material.

2. The method of claim 1, wherein the device further comprises a length of flexible tubing, the frangible container being disposed within the flexible tubing, and wherein the presenting step comprises coupling an end of the flexible tubing to a sampling nozzle of the chemical detector.

3. The method of claim 1, wherein the presenting step comprises:
   inserting the device into a length of flexible tubing to cause the frangible container to be disposed within the flexible tubing; and
   coupling an end of the flexible tubing to a sampling nozzle of the chemical detector.

4. The method of claim 1, wherein the released chemical material contacts a wicking material surrounding the broken frangible container to introduce chemical vapors to the chemical detector for validation.

5. The method of claim 1, wherein the predetermined amount of chemical material is sufficient to meet a threshold alarm level of the chemical detector.

6. A method for making a device to validate or calibrate a chemical detector at a point of use, comprising:
   supplying a predetermined amount of chemical material to a frangible container, the frangible container having first and second tubes coupled thereto at a first end, each of the first and second tubes having a second free end to define a substantially u-shaped vessel; and
   sealing the second free ends of the first and second tubes; and wherein the supplying step includes supplying the predetermined amount of the chemical material to the frangible container through the first tube and venting air from the frangible container through the second tube prior to sealing.

7. The method of claim 6, wherein the sealing step comprises sealing the second free end of the first tube and immediately thereafter sealing the second free end of the second tube.

8. The method of claim 6, further comprising wrapping the frangible container into at least one of a wicking material or a mesh material.

9. The method of claim 6, further comprising inserting the frangible container into a length of flexible tubing.

10. The method of claim 6, wherein the chemical material comprises at least one of a liquid chemical material or gaseous chemical material.

11. The method of claim 6, wherein the chemical material comprises a volatile or semi-volatile chemical material.

12. A device for validating or calibrating a chemical detector at a point of use, comprising:
   a frangible container defining a predetermined volume;
      a chemical material disposed within the frangible container in a predetermined amount, wherein the predetermined amount of chemical material is sufficient to meet a threshold alarm level of the chemical detector; and
      first and second tubes each having a first end coupled to the frangible container and a second free end to define a substantially u-shaped vessel, wherein each second end is sealed.

13. The device of claim 12, wherein the second end of the second tube is tapered.

14. The device of claim 12, wherein the first and second tubes have an inner diameter large enough to prevent the chemical material from remaining in the first or second tubes by capillary action.

15. The device of claim 12, wherein the frangible container comprises glass.

16. The device of claim 12, wherein the frangible container comprises an approximately spherical glass bulb.

17. The device of claim 12, wherein the predetermined volume of the frangible container is approximately 50 micro-liters.

18. The device of claim 12, wherein the predetermined amount of the chemical material is between approximately 5 micro-liters and approximately 100 micro-liters.

19. The device of claim 12, wherein the predetermined amount of the chemical material is approximately 20 micro-liters.

20. The device of claim 12, wherein the chemical material comprises a volatile or semi-volatile chemical material.

21. The device of claim 12, wherein the chemical material comprises a liquid chemical material.

22. The device of claim 21, further comprising a wick material surrounding the frangible container and adapted to wick the liquid chemical material after the first and second tubes are squeezed together to break the frangible container and release the liquid chemical material.

23. The device of claim 22, wherein the wick material is adapted to contain broken fragments of the frangible container after release of the liquid chemical material.

24. The device of claim 12, wherein the chemical material comprises a gaseous chemical material.

25. The device of claim 12, further comprising a mesh material surrounding the frangible container to contain broken fragments of the frangible container after release of the chemical material.

26. The device of claim 25, wherein the mesh material comprises a polymer mesh.

27. The device of claim 12, further comprising a length of flexible tubing, the frangible container being disposed within the flexible tubing, and wherein the flexible tubing is configured to be attached to a sampling nozzle of the chemical detector.

* * * * *